(12) United States Patent
Casse et al.

(10) Patent No.: US 10,307,607 B2
(45) Date of Patent: Jun. 4, 2019

(54) FOCUSED MAGNETIC STIMULATION FOR MODULATION OF NERVE CIRCUITS

(71) Applicant: Palo Alto Research Center Incorporated, Palo Alto, CA (US)

(72) Inventors: Bernard D. Casse, Saratoga, CA (US); Victor Liu, Mountain View, CA (US)

(73) Assignee: Palo Alto Research Center Incorporated, Palo Alto, CA (US)

(*) Notice: Subject to any disclaimer, the term of this patent is extended or adjusted under 35 U.S.C. 154(b) by 321 days.

(21) Appl. No.: 15/019,702

(22) Filed: Feb. 9, 2016

(65) Prior Publication Data

US 2017/0225004 A1 Aug. 10, 2017

(51) Int. Cl.
*A61N 2/02* (2006.01)
*A61N 2/00* (2006.01)

(52) U.S. Cl.
CPC .............. *A61N 2/006* (2013.01); *A61N 2/02* (2013.01)

(58) Field of Classification Search
CPC .................................. A61N 2/02; A61N 2/006
See application file for complete search history.

(56) References Cited

U.S. PATENT DOCUMENTS

| | | | |
|---|---|---|---|
| 3,951,134 A | 4/1976 | Malech | |
| 5,284,144 A | 2/1994 | Delannoy et al. | |
| 6,646,533 B2 | 11/2003 | Biegelson et al. | |
| 2004/0230263 A1 | 11/2004 | Samulski | |
| 2008/0275289 A1* | 11/2008 | Olree | A61N 2/02 600/13 |
| 2008/0284674 A1 | 11/2008 | Herz et al. | |
| 2009/0018384 A1* | 1/2009 | Boyden | A61N 2/02 600/13 |
| 2010/0028647 A1 | 11/2010 | Schneider et al. | |
| 2010/0286470 A1 | 11/2010 | Schneider et al. | |
| 2011/0199273 A1 | 8/2011 | Kim et al. | |
| 2011/0213195 A1 | 9/2011 | Kraus et al. | |
| 2011/0245900 A1 | 10/2011 | Turner et al. | |
| 2012/0065714 A1 | 3/2012 | Szasz et al. | |
| 2012/0101327 A1* | 4/2012 | Dissing | A61N 2/002 600/14 |

(Continued)

FOREIGN PATENT DOCUMENTS

| | | |
|---|---|---|
| CN | 102784436 | 11/2012 |
| EP | 2975693 | 1/2016 |
| EP | 2975694 | 1/2016 |

OTHER PUBLICATIONS

EP Search Report from EP App. No. 17153587.5 dated Jul. 3, 2017, 7 pages.
Bonmassar et al., "Optimizing Microscopic Magnetic Fields for Neuronal Stimulation", International Journal of Bioelectromagnetism, vol. 16, No. 1, 2014, pp. 1-31.

(Continued)

*Primary Examiner* — Thaddeus B Cox
(74) *Attorney, Agent, or Firm* — Hollingsworth Davis, LLC

(57) ABSTRACT

A neuromodulation device includes electrically conductive coils arranged in an array and circuitry coupled to energize the coils in the array using current pulses that generate an electromagnetic field. The circuitry is configured to control one or more parameters of the current pulses, including at least amplitude and phase of the current pulses, such that the electromagnetic field undergoes constructive and destructive interference that focuses and/or steers a magnetic flux density within a region of interest of a patient.

20 Claims, 15 Drawing Sheets

(56) References Cited

U.S. PATENT DOCUMENTS

| | | |
|---|---|---|
| 2012/0229339 A1 | 9/2012 | Higgins |
| 2013/0096363 A1 | 4/2013 | Schneider et al. |
| 2014/0257438 A1* | 9/2014 | Simon ................. A61N 1/0456 607/72 |
| 2014/0357935 A1* | 12/2014 | Ilmoniemi ............... A61N 2/02 600/13 |
| 2015/0080637 A1* | 3/2015 | Bonmassar ............ A61N 2/006 600/14 |
| 2015/0283395 A1 | 10/2015 | Sabouni |
| 2015/0328477 A1* | 11/2015 | Gale ....................... A61N 2/02 600/13 |
| 2016/0023016 A1* | 1/2016 | Bonmassar ............ A61N 2/006 600/13 |
| 2016/0166843 A1 | 1/2016 | Casse et al. |
| 2016/0220838 A1* | 8/2016 | Scheinowitz ............ A61N 2/02 |
| 2017/0014637 A1* | 1/2017 | Basser ..................... A61N 1/40 |
| 2017/0216594 A1 | 8/2017 | Grossman et al. |

OTHER PUBLICATIONS

Ge et al., "A Design of Array Transcranial Magnetic Stimulation Coil System", International Science Index, Biomedical and Biological Engineering, vol. 6, No. 5, 2012, 4 pages.

Rohde et al., "Focused High Frequency Repetitive Transcranial Magnetic Stimulation for Localisation of the Unexposed Primary Motor Cortex During Brain Tumour Surgery", Journal of Neurology, Neurosurgery & Psychiatry, Feb. 12, 2003; 74, 1283-1287.

File History for US. Appl. No. 14/567,604 as retrieved from the U.S. Patent and Trademark Office Pair System dated Jan. 10, 2019, 264 pages.

Dmochowski et al., "Noninvasive Neuromodulation Goes Deep", Cell, 169 (6), Jun. 2017, pp. 977-978.

Goats, "Interferential Current Therapy", Br. J. Sp. Med, vol. 24, No. 2, Jun. 1, 1990, pp. 87-92.

Grossman et al., "Noninvasive Deep Brain Stimulation via Temporally Interfering Electric Fields", Cell, 169, Jun. 1, 2017, pp. 1029-1041.

* cited by examiner

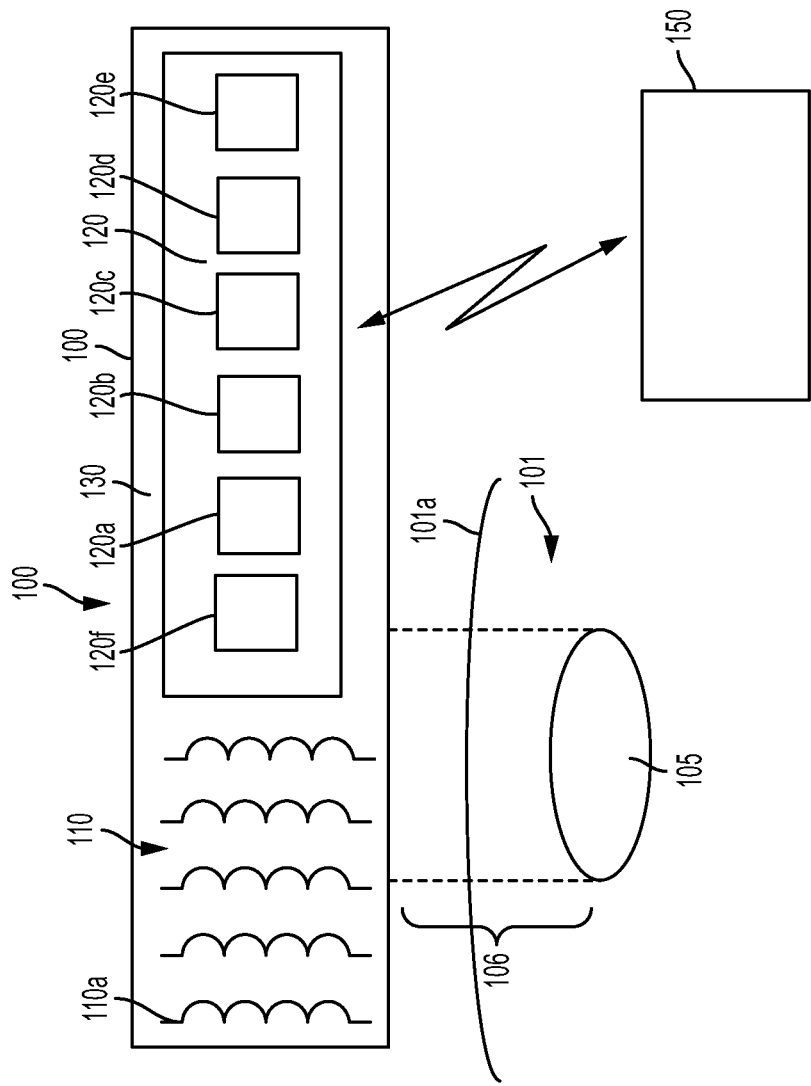

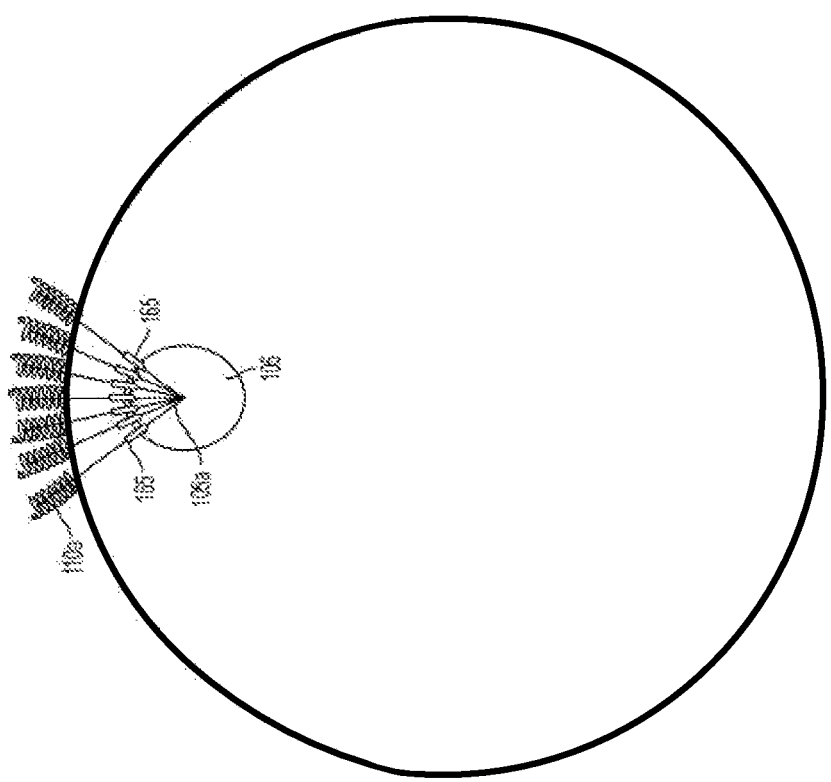

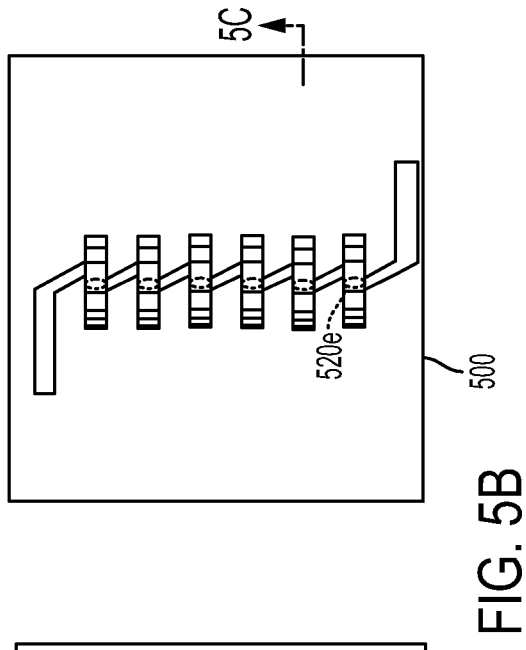
FIG. 5B
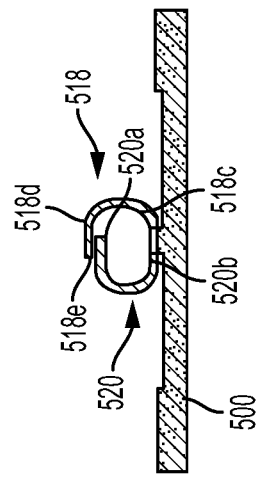
FIG. 5C
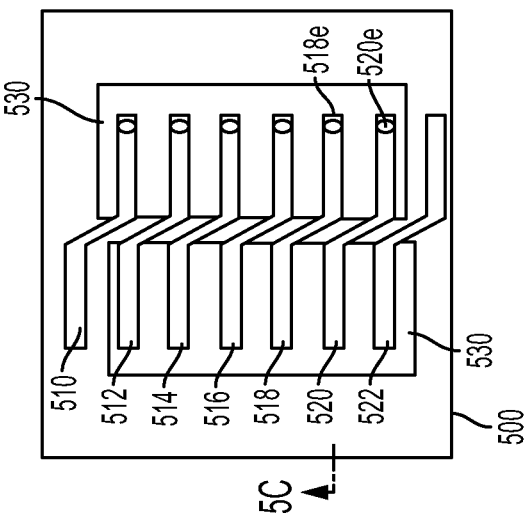

FOCUSED MAGNETIC STIMULATION FOR MODULATION OF NERVE CIRCUITS

TECHNICAL FIELD

This disclosure relates generally to devices, systems, and methods for modulation of nerve circuits by focused magnetic stimulation.

BACKGROUND

Neuromodulation is an evolving therapy that can involve various types of electromagnetic stimuli including the application of a strong magnetic field or a small electric current to nerve structures.

SUMMARY

Some embodiments are directed to a neuromodulation device that includes electrically conductive coils arranged in an array and circuitry coupled to energize the coils in the array using current pulses that generate an electromagnetic field. The circuitry is configured to control one or more parameters of the current pulses, including at least amplitude and phase of the current pulses, such that the electromagnetic field undergoes constructive and destructive interference that focuses and/or steers a magnetic flux density within a region of interest of a patient.

Some embodiments involve a neuromodulation system. The system includes a neuromodulation device comprising electrically conductive coils arranged in an array and circuitry coupled to energize the coils in the array with current pulses that generate an electromagnetic field. The circuitry is configured to control one or more parameters of the current pulses, including at least amplitude and phase of the current pulses, such that the electromagnetic field undergoes constructive and destructive interference that focuses and/or steers a magnetic flux density within a region of interest of a patient. Communications circuitry is configured to wirelessly transfer communication signals between the neuromodulation device and an external device. A patient information device is communicatively coupled to the neuromodulation device and is configured to monitor one or more biological signals of the patient and to transfer information about the biological signals to the neuromodulation device via the communication signals.

A neuromodulation method includes energizing coils in an array of coils using current pulses. The current pulses generate an a electromagnetic field that provides a magnetic flux density at a region of interest of a patient. One or more parameters of the current pulses, including at least amplitude and phase, are controlled such that the electromagnetic field undergoes constructive and destructive interference that focuses and/or steers the magnetic flux density to the region of interest.

BRIEF DESCRIPTION OF THE DRAWINGS

FIG. 1A is a block diagram of a neuromodulation device in accordance with some embodiments;

FIG. 1F illustrates manipulation the field strength of the electric field at a selected location by approximately adding the linear vectors of the individual fields in accordance with some embodiments;

FIGS. 5B and 5C illustrate a process for forming a stress engineered coil structure in accordance with some embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1B:
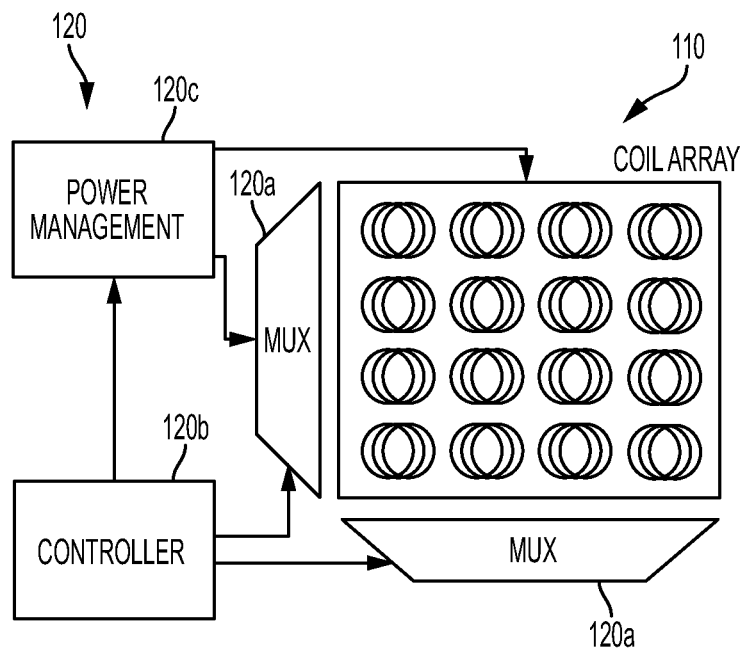
FIG. 1B illustrates a portion of the circuitry and coil array in accordance with some embodiments.

Up to 23% of patients with nerve stimulation devices experience surgery-related and/or other complications, hardware malfunctions, and/or adverse side effects. Many of these adverse outcomes are the result of one or more of the relatively large size of the nerve stimulation device, the invasive nature of surgical implantation, the relatively large, unfocused spread of electrical currents into off-target regions because of the inability of electric stimulation to reliably activate specific sections of the nerve, and the lack of a sensor-driven smart algorithms to provide feedback control to optimize stimulation. Current neuromodulation technologies stimulate large volumes including unwanted regions, and may not penetrate sufficiently below the skin surface. These limitations hinder the applications and effectiveness of classic neuromodulation technology, not only for brain stimulation, but also for modulating peripheral nerve circuits.

Approaches discussed herein are directed to high-precision spatial targeting of nerve circuits by shaping magnetic fields. The neuromodulation devices disclosed herein provide minimally-invasive and/or feedback-controlled neural modulation for regulating brain stimulation as well as regulating peripheral nerve circuits such as the vagus nerve. The ability to selectively stimulate nerve fascicles enables treatment of a wide-range of peripheral and central nervous system disorders with targeted therapies. The focused magnetic stimulation (FMS) neuromodulation approaches disclosed herein are underpinned by metamaterial coils as discussed below. These micro-engineered metamaterial structures allow for far greater control of electromagnetic fields over conventional transducer technologies. Driven by smart current distribution algorithms, FMS can non-invasively target small bundles of nerve fibers, as well as provide tailored stimulus patterns. The use of an array of metamaterial coils combined with a current distribution algorithm enables more localized stimulations, deeper penetration, enhanced depth control, and complex stimulation patterns with the ability to target specific nerve fascicles.

Turning now to FIG. 1 there is shown a neuromodulation device 100 configured to provide neuromodulation stimulation n. The neuromodulation device 100 may be useful for transcranial nerve stimulation as well as stimulation of the peripheral nerves, such as the vagus nerve, for example. The device 100 includes electrically conductive coils 110a arranged in an array 110 and circuitry 120.

The circuitry 120 includes multiplexer circuitry 120a configured to allow access to individual coils of the array 110; a controller 120b configured to control the parameters of the current pulses provided to energize the coils 110a; power management circuitry 120c configured to provide power for the current pulses; and driver circuitry 120f configured to energize the coils 110a in the array 110. In some embodiments, the circuitry 120 may include a battery and/or energy harvesting circuitry 120d that supplies energy to the power management circuitry 120c and communication circuitry configured to communicate with an external device 150.

The controller 120b is configured to control one or more parameters of the current pulses, including at least amplitude and phase of the current pulses, such that the electromagnetic fields produced by the coils 110a in the array 110 undergo constructive and destructive interference that focuses and/or steers a magnetic flux density within a region of interest 105 of a patient 101. In some embodiments, a neuromodulation device 100 may be an external therapy system that is placed on or above the skin 101a of the patient 101 as illustrated in FIG. 1A. In some embodiments, the neuromodulation device 100 may be at least partially implantable. For example, the coil array 110 and/or circuitry 120 may be implanted subcutaneously.

In some implementations, in addition the control of the amplitude and phase of the current pulses, the controller 120b may be configured to additionally additional parameters of the current pulses such as the duty cycle and/or frequency of the current pulses. Control of the current pulse parameters is used to focus and/or steer the magnetic flux density within the region of interest 105.

The coils 110a of the array 110 may have a diameter in a range of greater than or equal to about 100 µm to about 500 µm, or in a range of greater than or equal to about 10 µm to about 100 µm, for example. In some embodiments, the coils 110a are 2D planar coils and in some embodiments, the coils are 3D metamaterial coils made of one or more stressed elastic members as disclosed in commonly owned U.S. Pat. No. 6,646,533 which is incorporated by reference herein. The resolution of the stimulation head comprising array 110 may be about three times the diameter of one of the coils 110a in the array 110. In one example implementation, the neuromodulation device may comprise a 10×10 array of coils, each coil having a diameter of 150 µm, a coil pitch (center to center distance between coils) of 150 µm, a maximum stimulation area size of 3 mm², and current injection in each coil of less than 100 mA.

In some embodiments, the magnetic flux density within the region of interest 105 is greater than about 0.1 Tesla, the electric field strength within the area of interest 105 may be about Ex=dV/dx>100 V/m, an electric field gradient within the area of interest 105 may be about dEx/dx>500 V/m² and/or a maximum electric current pulse amplitude in each coil may be less than about 500 mA or even less than about 100 mA. In some implementations, the magnetic flux density, electric field strength and/or electric field gradient produced by the array 110 is sufficient to activate one or more neurons within the region of interest 105 to provide neuromodulation therapy. For example, the magnetic flux density, electric field strength, and/or electric field gradient produced by the array 110 within the region of interest 105 may be sufficient to activate a nerve fascicle at a specified depth within a nerve bundle while not activating other nerve fascicles of the nerve bundle. In some scenarios, the neuromodulation therapy may involve using the array 110 to provide a magnetic flux density, electric field strength, and/or electric field gradient at a sub threshold level that is below the activation threshold of the nerve fibers in the region of interest.

The region of interest 105 is located at a specified depth within the patient 101 and the magnetic flux density, electric field strength, and/or electric field gradient produced by the neuromodulation device 100 in a region 106 between the region of interest 105 and the array 110 is less than the magnetic flux density, electric field strength, and/or electric field gradient in the region of interest 105.

Optionally, the neuromodulation device 100 includes a substrate 130, wherein the array 110 of coils 110a and the circuitry 120 are disposed on the substrate 130. The substrate 130 can be flexible. For example, in various embodiments, the substrate 130 may comprise an implantable nerve cuff or a dermal patch. In some implementations, the neuromodulation device can be printed on a flexible substrate.

In some embodiments, the neuromodulation device 100 includes power supply circuitry that optionally comprises a battery. In some embodiments, the power management circuitry 120c obtains power from a power supply 120d such as a battery or energy harvesting circuit. When present, the energy harvesting circuit is configured to harvest power from a radio frequency (RF) signal generated by an additional device 150 which may be a patient-external device. The power supply 120d provides power to the power management circuitry 120c which uses the harvested power to provide the current pulses to the coils 110a.

In some embodiments, the neuromodulation device includes communications circuitry 120e configured to wirelessly transfer communication signals between the neuromodulation device 100 and an additional device 150. The device 150 may be configured to obtain biological information from the patient wherein the biological information is used to develop feedback information for the FMS. In some scenarios, the communications signals passed between the device 150 and the communications circuitry 120e include the feedback information and the controller 120b uses the feedback information to control the current pulse parameters.

In some embodiments, the controller 120b includes a memory that stores one or more tables of current pulse parameter values for each coil in the array, each table corresponding to a particular profile of biological information that is consistent with the current physiological state of the patient. The current physiological state of the patient may be provided to the controller 120b by the external device 150 via the communications circuitry 120e. The controller 120b accesses the memory to retrieve the current pulse parameter values to be used for the stimulation, wherein the current pulse parameter correspond to the patient's physiological state. In some implementations, the current pulse parameter values utilized by the neuromodulation device are dynamically changeable in response to a change in the biological information obtained from the patient via device 150. The circuitry 120 may be implemented using a silicon based application specific integrated circuit (ASIC) and/or a thin-film-transistor (TFT) circuitry backplane. TFT implementation is particularly useful for flexible substrates.

Each coil 110a in the array 110 may be individually addressable, e.g., using multiplexers 120a and the controller 230b, to implement an addressable array. Each coil 110a is coupled to driving circuitry 120f. In some implementations, the driving circuitry 120f may support bipolar currents by incorporating a pair of complementary transistors as shown in FIG. 1C. Driving circuitry 120f allows programming of a distinct current through each coil 110a before the entire array 110 is activated.

Figure 1C:
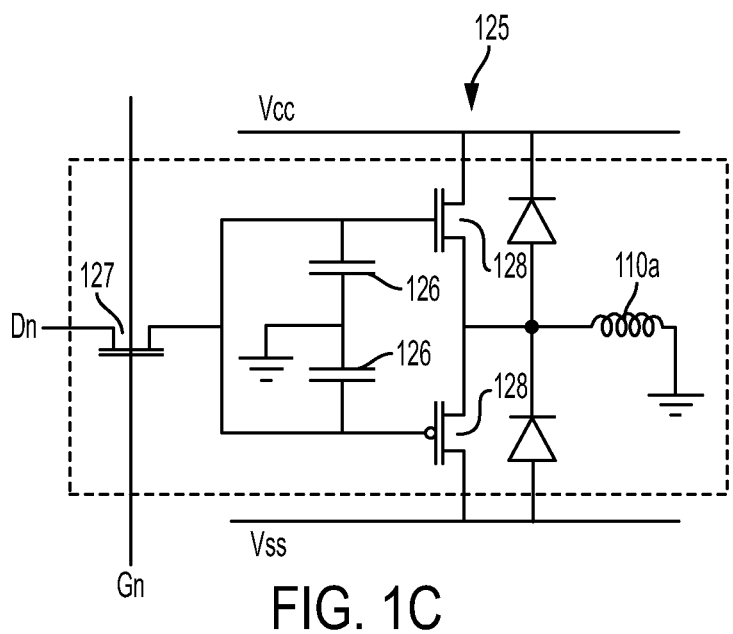
FIG. 1C illustrates the driver circuitry for each coil in accordance with various embodiments.

FIG. 1B illustrates a portion of the circuitry 120 and coil array 110 in accordance with some embodiments. FIG. 1C illustrates the driver circuitry 120f for each coil 110a. As illustrated in FIG. 1B, circuitry 120 includes a controller 120b and row and column multiplexers 120a configured to access the array coils 110a. The circuitry 120 further includes power management circuitry 120c that operates in conjunction with the controller 120b and multiplexers 120a to implement the current pulse injection algorithm. The current pulse injection algorithm provides the current distribution in the coils 110a to enable high-precision targeting and/or to tailor stimulus patterns. For example, the current pulse injection algorithm may implement a phased array stimulation wherein coils 110a are selectively energized by current pulses that are in phase and/or out of phase to provide constructive and/or destructive interference between the electric fields generated by at least some of the coils 110a of the array 110. The constructive and/or destructive interference in the electric fields generated by the coils allows more localized stimulations, deeper penetration, depth control, and complex nerve stimulation patterns.

The controller 120b provides signals to the multiplexers 120a for selection of the column and row of the coil array 110. The controller 120b controls the power management circuitry 120c for providing a value for a particular coil driver circuitry 120f shown in FIG. 1C. The value of Dn determines the amplitude of the current pulse. The timing of the application of Vss and Vcc to a coil driver (see FIG. 1C) by the power management circuitry 120c is also controlled by the controller 120b and determines the phase, duty cycle, and/or frequency of the current pulses provided by the driver circuitry 120f to the coil 110a.

Referring now to FIG. 1C, to program a particular coil, Vcc and Vss are set to zero. A particular column of the array 110 is activated by applying a voltage to Gn and a value Dn is applied to the transistor 127 to set the pulse amplitude value in the gate capacitors 126 for the coil 110a. The proper bias voltage is set on Dn for the appropriate amount of current that the coil requires, which may be positive or negative.

To activate the coil 110a, Gn and Dn are disabled and Vss and Vcc, e.g. Vss=−5V and Vcc=+5V, are applied to the driver circuit 120f for a duration commensurate with the stimulation parameters. Bipolar operation is enabled by connecting the pair of capacitors 126 to the complementary pair of transistors 128. The coils 110a in the array are addressed by a TFT backplane similarly to the way that liquid crystals are addressed by a TFT backplane in a display, utilizing gate and data line multiplexers. The onboard power supply is capable of providing the full range of positive and negative bias voltages for the array, and the controller provides the signals required for activating individual "pixels" in the array and for activating the supply rails.

Figure 1D:
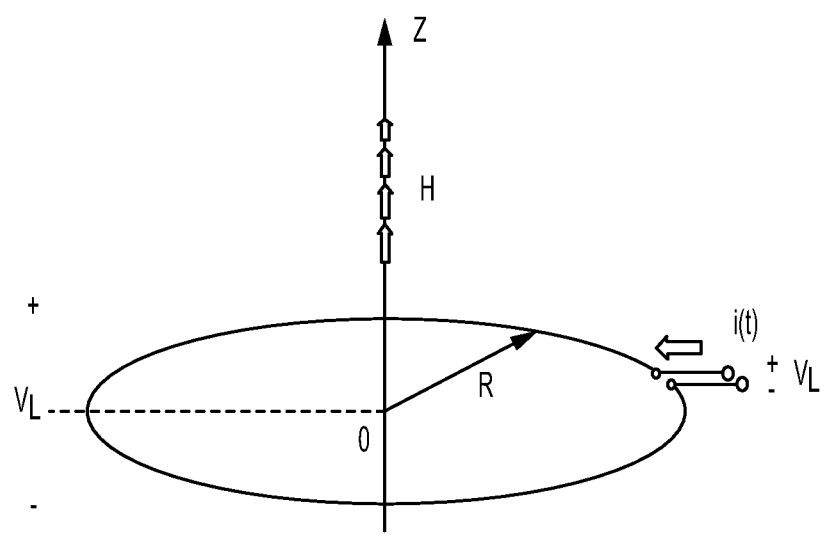
FIG. 1D illustrates the magnetic field created by a single loop coil.

The current pulse through the coils 110a generates a magnetic field. Referring now to FIG. 1D, which shows a single loop coil, and Equation (1), the magnetic field created by each loop, $H_z^{LOOP}$, increases with the radius of the loop, R, and the intensity of the current, i(t), and decreases with the distance, z, along the axis.

$$H_z^{LOOP}(z) = \frac{\frac{1}{2}R^2 i(t)}{(R^2 + z^2)^{1/2}} \quad (1)$$

Figure 1E:
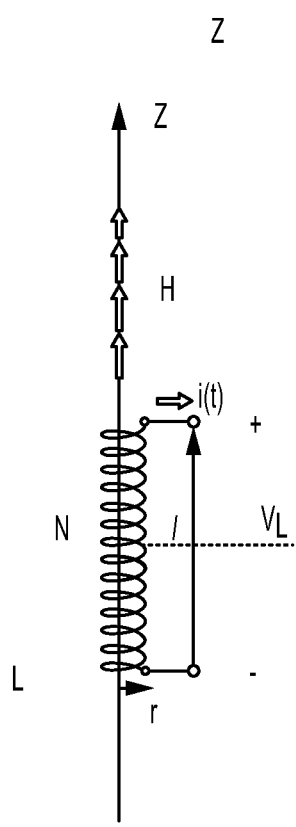
FIG. 1E illustrates the magnetic field created by a multi-loop coil.

The magnetic field of a coil depends on the number of turns, N, the length, l, the pitch, α, and the amplitude of the current as indicated by FIG. 1E, which shows a small radius coil, and Equation (2). By increasing N (or the inductance of the coils), and l, we can considerably increase the resulting magnetic field even for a fixed low current and small radius coil, as deduced from Equation (1). Thus, arranging a large number of small coils in an array configuration, as shown in FIG. 1E will yield an increase in the magnetic field intensity and penetration to specific regions.

$$H_z^{COIL}(z) = \frac{i(t)}{4\pi r \tan\alpha} \left\{ \frac{N\pi r \tan\alpha + z}{\sqrt{r^2 + (N\pi \tan\alpha + z)^2}} + \frac{N\pi \tan\alpha - z}{\sqrt{r^2} + \sqrt{r^2 + (N\pi \tan\alpha - z)^2}} \right\} \quad (2)$$

FIG. 1F is a schematic representation of beam focusing and beam steering within a region of interest 105. As illustrated in FIG. 1F, since each coil 110a is driven by a coil current that is independent of other coil currents, it is possible to manipulate the field strength of the electric field at a selected location, such as the focal point 105a within region of interest 105, by approximately adding the linear vectors 165 of the individual fields. Thus, tailored stimulations can be obtained with appropriate coil array designs, by selecting the optimal number of elements, array configuration, driving circuits, and current distribution in the coils.

Figure 2:
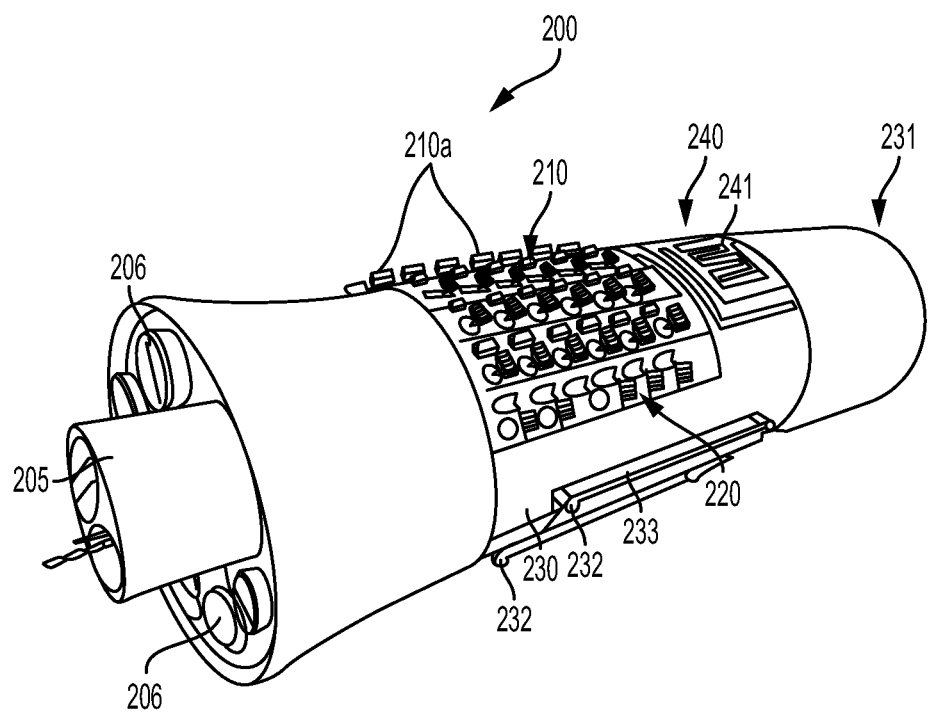
FIG. 2 illustrates an embodiment of the neuromodulation device wherein the device is disposed on a flexible substrate configured as an implantable nerve cuff in accordance with some embodiments.

FIG. 2 illustrates an embodiment of the neuromodulation device 200, wherein the device 200 is disposed on a flexible substrate 230 configured as an implantable nerve cuff. The flexible substrate 230 is configured to at least partially surround a nerve bundle 231 and is sutured in position around the nerve bundle 231 via sutures 233 attached to suture anchors 232 located on the flexible substrate 230. The device 200 includes electrically conductive coils 210a arranged in an array 210 and circuitry, e.g., as described in FIGS. 1A-1F, coupled to energize the coils 210a in the array 210 using current pulses that generate an electromagnetic field. The current pulses provided to the coils 110a by the circuitry activates the coils 110a and creates a tailored magnetic field 220 within the nerve bundle 230. The circuitry is configured to control one or more parameters of the current pulses, including at least amplitude and phase of the current pulses, such that the electromagnetic field undergoes constructive and destructive interference that focuses and/or steers the electric field within a region of interest of a patient.

In the embodiment shown in FIG. 2, the region of interest includes the nerve fascicle 205 and does not include nerve fascicles 206. The magnetic flux density, electric field strength and/or electric field gradient produced by the array 210 is sufficient to activate one or more neurons within the region of interest to provide neuromodulation therapy. For example, the magnetic flux density, electric field strength, and/or electric field gradient produced by the array 210 may be sufficient to activate the nerve fascicle 205 at a specified depth and/or location within the nerve bundle 231 while not activating other nerve fascicles 206 of the nerve bundle 230. In some scenarios, the neuromodulation therapy may involve using the array 210 to provide a magnetic flux density, electric field strength, and/or electric field gradient to the nerve fascicle 205 at a sub threshold level that is below the activation threshold of the nerve fascicle while not providing the lower magnetic flux density, electric field strength, and/or electric field gradient to the other nerve fascicles 206 of the nerve bundle 230.

The neuromodulation device 200 includes a power supply 240 that optionally includes a battery. In some embodiments, the power supply 240 comprises at least one energy harvesting component, such as antenna 241, configured to harvest power from a radio frequency (RF) signal generated by an external device (not shown in FIG. 2). The power supply 240 provides power to the circuitry which uses the harvested power to provide the current pulses to the coils 210a.

Figure 3:
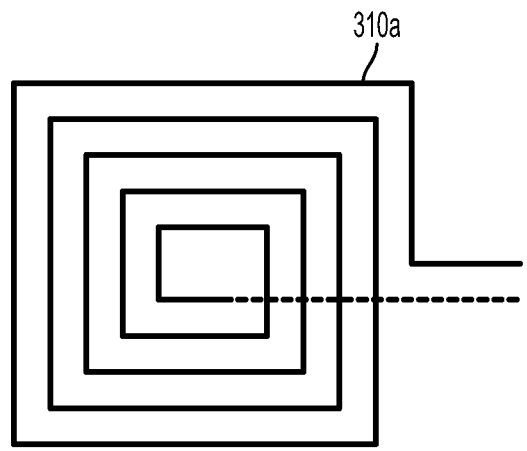
FIG. 3 illustrates a two dimensional flat planar coil that may be used in the coil array the neuromodulation device in accordance with some embodiments.

The coils 210a shown in FIG. 2 are 3D coils. In some embodiments, the device may use coils that are flat planar coils 310a disposed on the substrate as shown in FIG. 3. In some embodiments, the coils 210a are three dimensional coils comprising an out-of-plane micro-structure. The three dimensional coils shown in FIG. 4, for example, can be used for the array and enable a magnetic field in a direction parallel to the substrate plane without requiring high aspect ratio processing.

Figure 4:
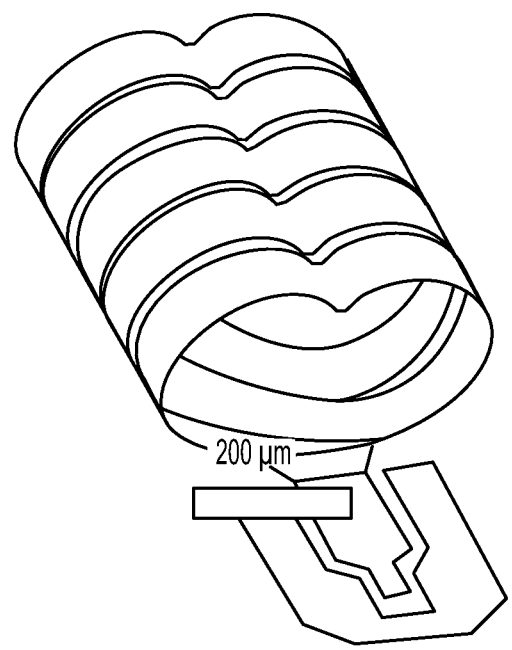
FIG. 4 shows a three dimensional coil that may be used in the coil array the neuromodulation device in accordance with some embodiments.

The scanning electron micrograph in FIG. 4 shows an out-of-plane micro-coil in accordance with some embodiments. The coil windings may be made using stress engineered thin films that are deposited by sputtering. The film is photolithographically patterned into strips of microsprings or elastic members that are subsequently released from their underlying substrate. Upon release, a built-in stress gradient causes the elastic members to curl and form three-dimensional out-of-plane loops that make up the inductor coil. In the coil shown in FIG. 4, the free end each of each member contacts an adjacent member. This allows for the formation of a continuous inductor consisting of multiple turns without interruption of the spring metal. To protect the inductor in actual use on a chip or circuit board, the loops can be enclosed in a molding compound. These coils can be mass-produced on prefabricated circuit wafers prior to dicing, bonding, and packaging.

Figure 5A:
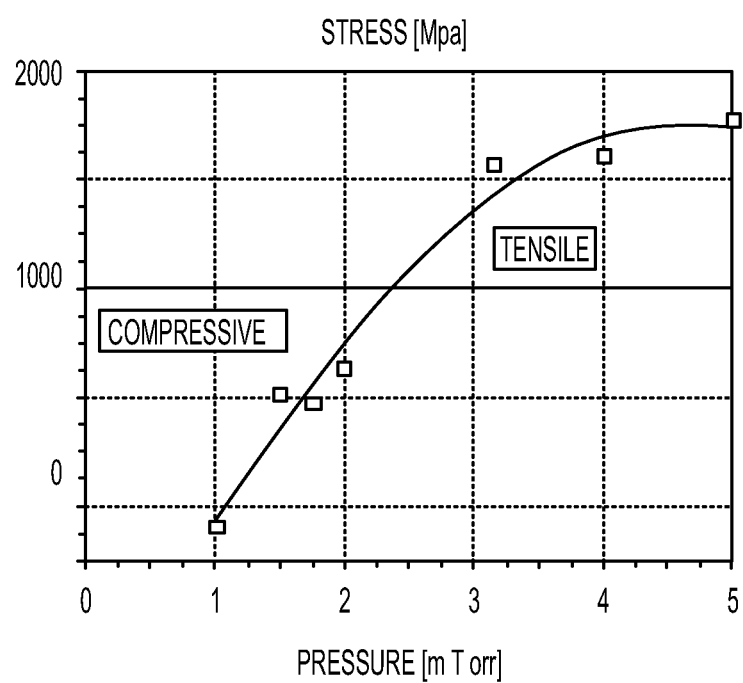
FIG. 5A shows a measured stress versus sputter pressure plot for MoCr.

In some embodiments, the coils are formed from stress-engineered molybdenum-chromium (MoCr) thin films. The MoCr films are sputter-deposited with a built-in stress gradient so that, when patterned and released from their substrate, they curl into a designed radius of curvature. These micro-machined springs self-assemble 3D scaffolds that are then electroplated with copper to form highly conductive coil windings. The coil arrays can be integrated onto silicon die that also include other circuit elements. Many refractory metals have a common property of acquiring tensile stress when sputtered at high pressures and compressive stress when sputtered at low pressures. This results in a stress gradient that can be induced by changing the ambient pressure during film deposition. A film that is compressive at the bottom and tensile on the surface is, for example, realized by increasing the pressure during sputtering. Pressure control may be accomplished by flowing argon while widening or narrowing an orifice opening to the pump. FIG. 5A shows a measured stress versus sputter pressure plot for MoCr.

FIGS. 5B and 5C show a process of forming an out-of-plane coil structure in which two half loops are closed in mid-air forming a loop winding in accordance with some embodiments. A layer of release material 530 is deposited on substrate 500 (for sequential release, two different release layers formed of different release materials may be deposited). Then a layer of an elastic material is deposited on top of the release layer 530. The elastic layer is photolithographically patterned into a series of individual elastic members 510-522. Each individual elastic member includes a first elastic member (e.g., 520a-520b), a contact portion or bridge for connecting between adjacent loop windings (e.g., 520b-520c) and a second elastic member (e.g., 520c-520d). A layer of solder (e.g., 520e) is optionally formed on the tip of the second elastic member.

The loop winding is formed by removing the release window under each first elastic member and each second elastic member. This can be done at the same time, or sequentially, by using a different release material under all the first elastic members than under all the second elastic members. Referring to FIG. 5C, release of the release layer under the first elastic member 520a-520b causes a first free portion 520a of the first elastic member to be released from the substrate 500. A first anchor portion 520b of the first elastic member remains fixed to the substrate. An intrinsic stress profile in the first elastic member biases the free portion 520a away from the substrate 500. Similarly, release of the release layer under the second elastic member 518c-518d causes a free portion 518d to be released from the substrate 500. An intrinsic stress profile in the second elastic member biases the free portion 518d away from the substrate 500. A second anchor portion 518c remains fixed to the substrate 500. Pressing and heating causes the solder 518e to reflow and join free end 520a to free end 518d.

Alternatively, and preferably, the free portions (without solder) can be connected together by electroless plating. Immersion in a plating bath and depositing metal on accessible metal surfaces both thickens all metal lines and creates bridges between proximal surfaces (such as contact portion 520b-520c).

The individual loop halves are shown in FIG. 5B as being of approximately the same length. However, the lengths can be varied to aid in the coil formation process. For example, the first elastic members can be made shorter than the second elastic members to ensure that the second elastic members overlap the first elastic members.

FIGS. 6A through 6D illustrate fabrication of the coil array in accordance with some embodiments. As seen from FIG. 5A, sputter pressures below 2.35 mTorr produce compressive MoCr films, while higher deposition pressures produce tensile films. When patterned and released, such a stress-graded film curls up in a circular trajectory with a radius of curvature given by:

$$r = h\frac{Y}{\Delta\sigma} \quad (3)$$

where h is the thickness, Y the biaxial Young's modulus, and Δσ is the stress difference between the surface and bottom of the film.

Figure 6A:
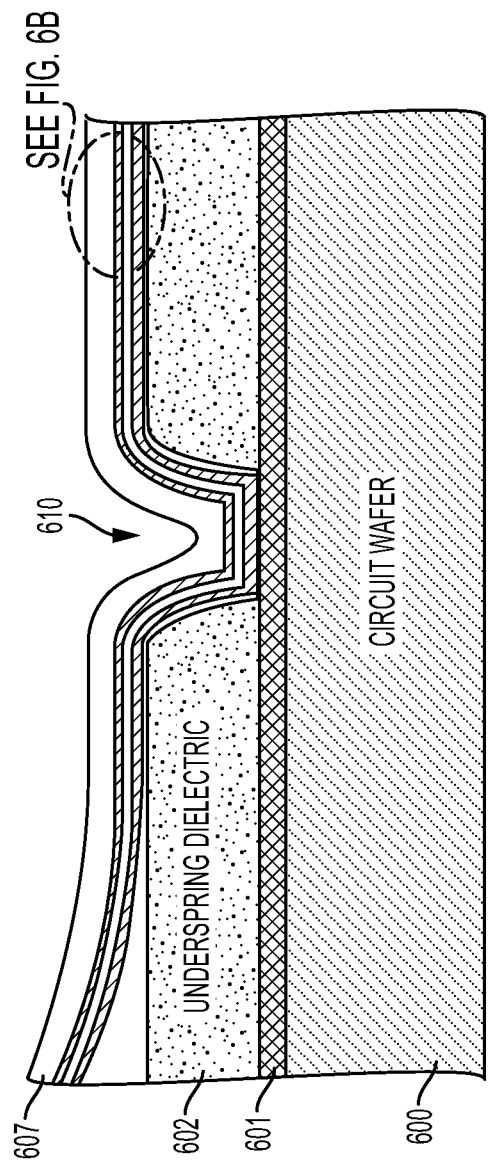
FIGS. 6A through 6C illustrate a process for forming a stress engineered coil structure in accordance with some embodiments.
Figure 6B:
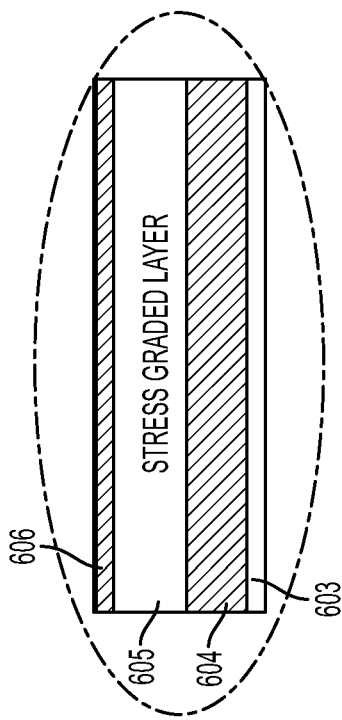

FIG. 6A is a cross sectional diagram of layers used to form the coils in the array and FIG. 6B is a more detailed view of some of the layers. In this embodiment, fabrication of the coil array starts with the deposition of a metal layer 601, e.g., a Cu-plated or gold metal layer on top of the substrate 600. The metal layer 601 serves as a current return path for the coil after it is completed. A 12 to 15 μm-thick low-loss dielectric layer 602 is spin-coated to separate the coil from the substrate and to lower its parasitic capacitance. Vias 610 to the underlying metal layer 601 are then opened. A conductive release/sacrificial layer 603 (not shown in FIG. 6A but shown in FIG. 6B) may be sputter deposited next, followed by a thin layer of metal 604, e.g., Au, (also not shown in FIG. 6A but shown in FIG. 6B), the stress engineered MoCr film 605 already described, and a passivation layer 606, e.g., an Au passivation layer. This stack is about 1.5 μm thick and the layers 601-606 are deposited sequentially in a single pump down. An electrically conductive release layer 603 may be used which is also used as an electrode for electroplating the windings after coil assembly, as will be discussed. The release material has excellent adhesion properties and also functions as an adhesion layer for the stressed films deposited above it. The stress-engineered film 605 is a bi-layer with the first MoCr layer deposited at low pressure on the compressive side of the graph in FIG. 5A, and the second MoCr layer at a higher pressure on the tensile side of the graph. The resulting built-in stress gradient produces a well-defined mechanical moment on the film. The Au/MoCr/Au 604/605/606 metal stack is patterned into individual springs that ultimately make up the coil windings. The intrinsic stress of many sputtered thin films depends on the ambient pressure at which the material is deposited. By varying the pressure during sputtering, films can be obtained that are compressively stressed near the substrate-film interface and tensile stressed at the film surface. FIG. 6B shows such a stress-graded film 605 sandwiched between two gold layers 604, 606. The stress graded film can be NiZr, MoCr, solder-wettable Ni, or other suitable material. The bottom gold layer 604 forms the outer skin of the coil when released and provides a high conductivity path for electrons at high frequencies. The top gold layer 606 passivates the surface. The metal stack is deposited above a suitable release layer 603 such as Ti, Si, or SiN. The release layer should be a material that can be quickly removed by selective dry or wet undercut etching. Possible etchants for a Si release layer include KOH (wet processing) and XeF2 (dry processing).

Figure 6C:
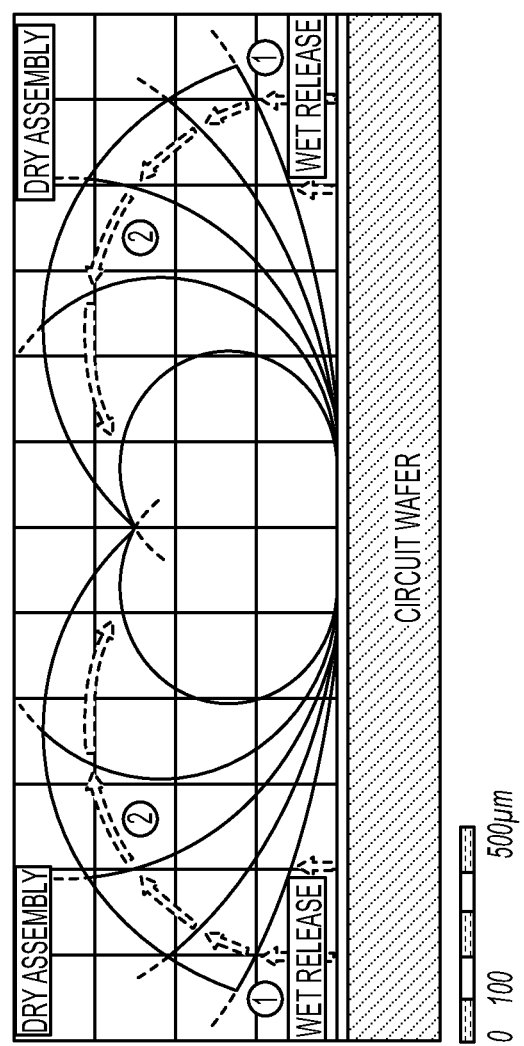
Figure 6D:
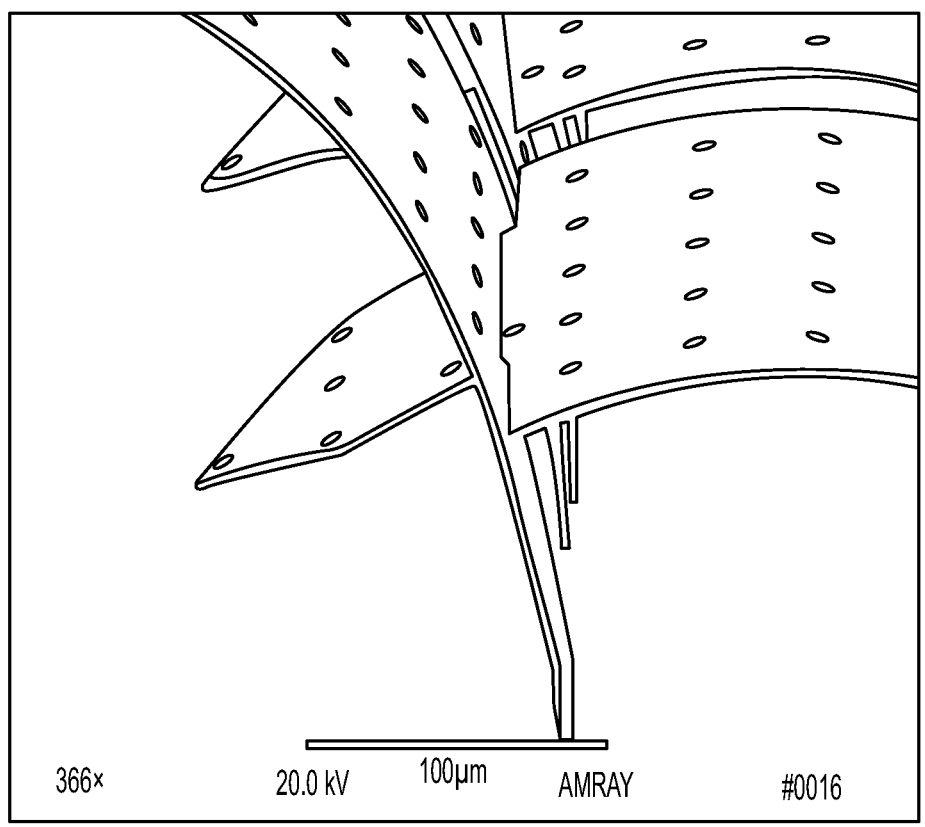
FIG. 6D shows interlocking tips of the coil loops in accordance with some embodiments.

After defining the release masking windows, the springs are released from the substrate by undercut etching the sacrificial layer. Perforations in the spring metal facilitate the undercut release process. The release mask is designed so that a piece of the photoresist 607 is retained on top of each spring after release. This resist material 607 acts as a relaxable load that retains the springs and prevents the coils from lifting fully during the release process. As shown in FIG. 6C, when heated, the load layer 607 softens and gradually yields to the built-in stress moment in the spring metal, allowing spring pairs to move in a designed trajectory while self assembling in the air.

In some embodiments, the coil structure features an interlocking spring tip that provides a mechanical block that prevents paired springs from curling further after they come together. The interlocking connection of the out-of-plane coil magnified in FIG. 6D ensures that the coil diameter is determined by mask design, rather than by the built-in stress. This is desirable because it relaxes the tolerance requirements on the stress profile in the stress-engineered film. Once assembled, the devices are sufficiently robust for handling in and out of plating solutions without coming apart. The assembled structure serves as a three-dimensional scaffold for copper plating. MoCr is a poor electrical conductor, a 5 to 8 μm thick copper skin is electroplated on the scaffold to form low resistance coil windings. The gold finish in the spring metal stack functions as a plating seed. The copper plating not only fills the spring perforations but also electroforms the interlocked seam, joining paired springs to a solid and permanent connection. After plating, the release mask is removed and all remaining release material is cleared. The completed devices are rugged and survive die drops on hard surfaces from heights of over 1 m. This four-mask coil process is compatible with wafer-scale processing and uses conventional sputter deposition techniques, standard photolithography, and simple wet etching techniques. The coils can be seamlessly integrated with other COMES circuitry from single or multiple foundry runs. The intrinsic stress profile in the elastic members discussed above can be designed into a thin film by varying the growth conditions appropriately during deposition to produce coil structures. By adding one or more conductive layers, a coil structure suitable for use as an inductor may be manufactured.

The 3D coils discussed in connection with FIGS. 5 and 6 are metamaterial structures having an intrinsic stress profile. Such metamaterial micron-scale coils allow far greater control of electromagnetic fields as compared with conventional transducer technologies. As understood in the art, the term "metamaterial structure" identifies an artificially engineered structure formed by two or more materials and multiple elements that collectively generate desired electromagnetic properties. A metamaterial structure achieves the desired properties not only from its composition, but also from the exactingly-designed configuration (e.g., the precise shape, geometry, size, orientation and arrangement) of the structural elements formed by the materials of the metamaterial structure.

Additional information regarding coils that are suitable for use in the devices and systems discussed herein and their methods of manufacture can be found in commonly owed U.S. Pat. No. 6,646,533 which is incorporated herein by reference.

The current pulse injection algorithm used in conjunction with the coils optimizes the current distribution in the coils to enable high-precision targeting and/or to provide tailored stimulus patterns. The current pulse injection algorithm is implements a phased array stimulation wherein coils are selectively energized to provide constructive and/or destructive interference between the electric fields generated by at least some of the coils. The constructive and/or destructive interference in the electric fields allows more localized stimulations, deeper penetration, depth control, and complex nerve stimulation patterns.

Figures 7A, 7B, 7C:
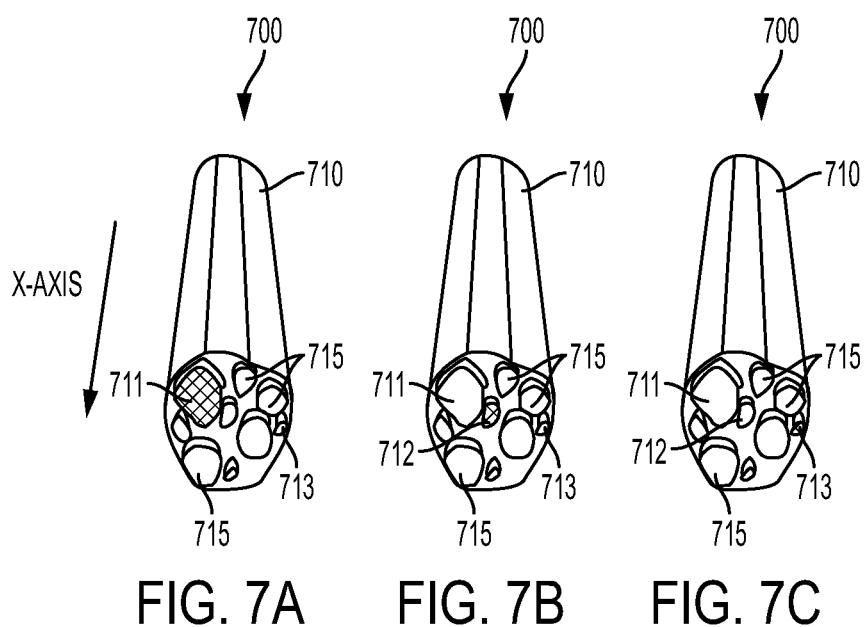
FIGS. 7A through 7C illustrate focused magnetic stimulation that is enabled by the neuromodulation devices and systems as described in embodiments herein.

FIGS. 7A through 7C illustrate focused magnetic stimulation that is enabled by the devices and systems described herein. FMS can be designed to target and activate nerve fascicles 711, 712, 713 in specific regions of a nerve bundle 710 without targeting other nerve fascicles 715 in the nerve bundle 710 demonstrating a level of control that is inaccessible to direct stimulation electrode technologies. In FIGS. 7A-7C, nerve fascicles 711-715 have an average diameter of about 150 µm. In FIG. 7A, the neuromodulation device 700 creates an electric field (E-field) such that nerve fascicle 711 experiences a spatial gradient of the E-field in the x-axis of greater than about 500 V/m² which activates nerve fascicle 711 while nerve fascicles 712, 713, 715 experience spatial gradient of the E-field in the x axis of less than 500 V/m², e.g., about 0 V/m² and are not activated. In FIG. 7B, the neuromodulation device 700 creates an electric field (E-field) such that nerve fascicle 712 experiences a spatial gradient of the E-field in the x-axis of greater than about 500 V/m² which activates nerve fascicle 712 while nerve fascicles 711, 713, 715 experience spatial gradient of the E-field in the x axis of less than 500 V/m², e.g., about 0 V/m² and are not activated. In FIG. 7C, the neuromodulation device 700 creates an electric field (E-field) such that nerve fascicle 713 experiences a spatial gradient of the E-field in the x-axis of greater than about 500 V/m² which activates nerve fascicle 713 while nerve fascicles 711, 712, 715 experience spatial gradient of the E-field in the x axis of less than 500 V/m², e.g., about 0 V/m² and are not activated.

The approaches described herein provide for steering and focusing the E-field (E) produced by coil array, e.g., a 4×1 or 2×2 coil array, in a region of interest using constructive and destructive interference. The E-field generated by each coil is controlled by the amplitude and phase of the current pulses that energize the coil. In some implementations, the E field generated by coils constructively interferes to create an area within the region of interest having an electric field that is greater than 200 V/m and less than about 50 V/m. The electric field distribution may have a spot size of about 400 µm. The resolution of the stimulation head of the neuromodulation device is dependent on the coil dimensions, e.g., the resolution is about equal to the diameter of coil×3.

Figure 8:
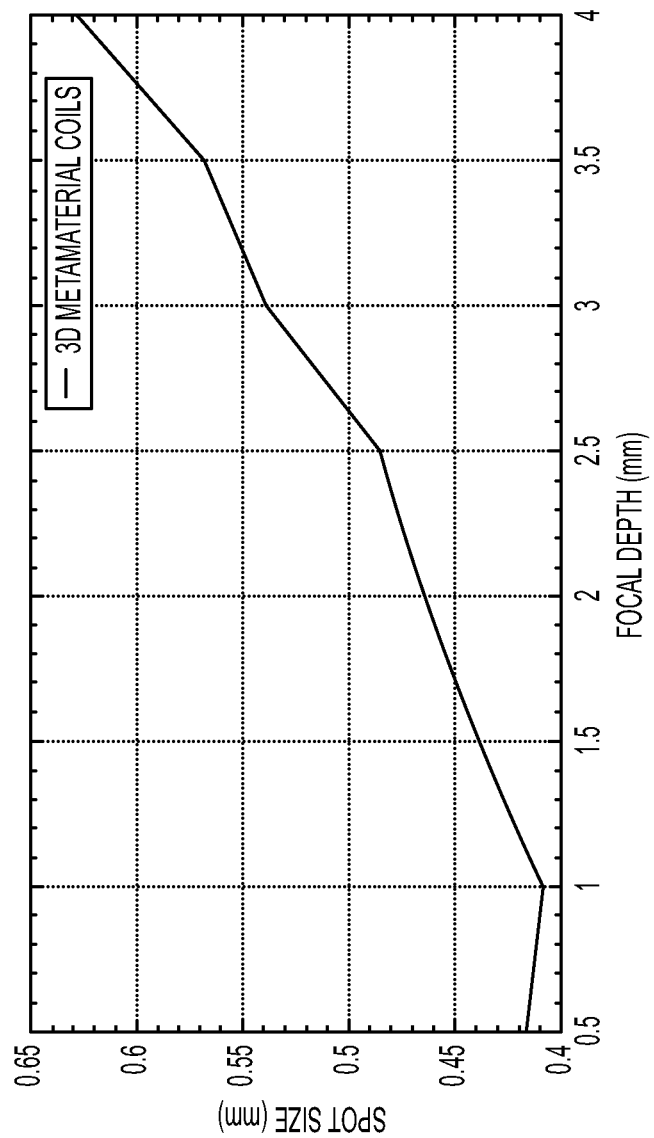
FIG. 8 is a plot of focal depth vs. spot size that is achievable using the neuromodulation devices according to embodiments described herein.

The electric field manipulation is achieved by modifying the intensity and relative phase of the currents in each coil in the array. By altering the current intensity and phase of individual coils, the ability to stimulate various depths (depth control) may be achieved, as shown in FIG. 8. In this simulation, the algorithm optimizes the current distribution at each targeted focal depth to minimize the stimulation spot size. As shown in FIG. 8 a spot size down to about 400 µm at a focal depth of about 1 mm is achievable using a phased array of 3D metamaterial coils as disclosed herein.

As previously discussed, the neuromodulation device disclosed herein may be used in a system that includes a patient information device configured to obtain information about patient conditions. The patient condition information may be obtained through sensors and/or may be input into the patient information device by the patient or other operator.

In some configurations, both the neuromodulation device and the patient information device may be a patient-external devices. For example, the neuromodulation device may be a dermal patch and the patient information device may be a patent-external device that communicates with the neuromodulation device through a wired or wired connection. In other configurations, both devices may be patient-internal, e.g., the neuromodulation device may be disposed on an implantable nerve cuff as illustrated in FIG. 2 and the patient information device be an implantable diagnostic or therapeutic device, such as a cardiac pacemaker, that wirelessly communicates with the neuromodulation device.

Figure 9A:
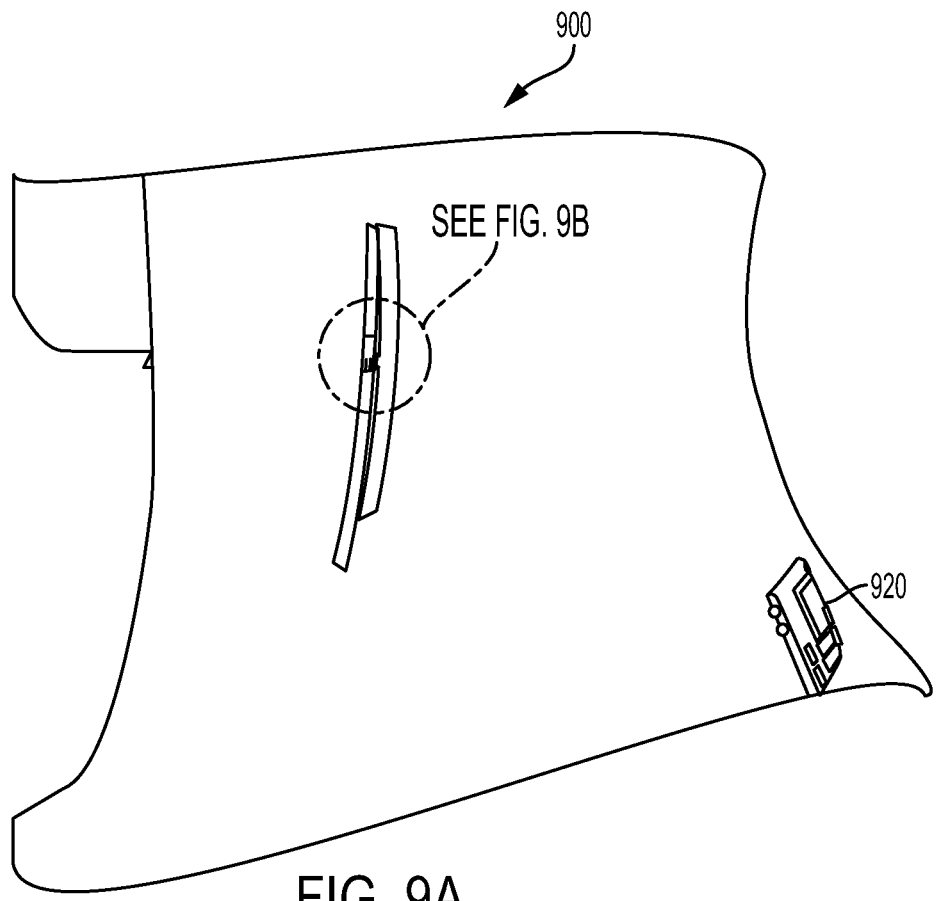
FIGS. 9A and 9B show a patient-internal neuromodulation device used in conjunction with a patient-external patient information device in accordance with some embodiments.
Figure 9B:
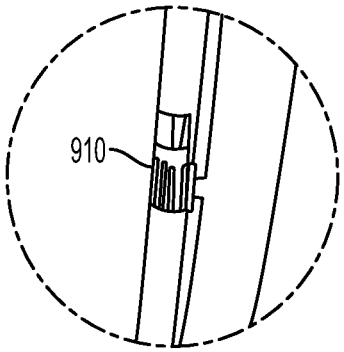

In yet other configurations, as shown in FIGS. 9A and 9B, the system may include a neuromodulation device 910 which is a patient-internal device and a patient-external patient information device 920 configured to wirelessly communicate with the neuromodulation device. In some embodiments, the patient information device 920 may be attached to the patient's skin as shown.

For example, the neuromodulation device 910 may be installed using an endovascular approach on the patient's vagus nerve. The patient information device 920 may comprise a sensing/control module that monitors dynamically changing physiological patient conditions, e.g., heart rate, respiration rate, blood pressure, body temperature etc. The patient information device 920 may sense the physiological state of the patient and generate feedback control signals that are communicated wirelessly to the neuromodulation device 910. In response to the feedback control signals, the neuromodulation device 910 alters one or more parameters of the current pulses that energize the coils. The feedback control of the patient information device 920 may synthesize and analyze both stimulation and sensing data by utilizing self-learning algorithms, and may be configured to adapt in real-time to enhance therapeutic efficacy.

In some embodiments, the patient information device measures biological signals such as heart rate (HR), blood pressure (BP), respiratory rate (RR), body temperature, etc., non-invasively. The patient information device develops a dynamic profile of biological signals in response to focused magnetic stimulation of the selected nerve. Spectral analysis of HR, BP, and RR may be performed to evaluate sympathetic and parasympathetic nervous system contributions. Optimal profiles of biological conditions that provide accurate feedback control for the stimulator function may be developed for each type of nerve stimulated. The optimal profiles may be based on data from a patient population or on individual patient responses to stimulation. The patient information device may be configured to adaptively regulate nerve circuits by continuously assessing the response to the stimulus provided by the stimulator module and reacting accordingly. The patient information device may be configured to use stimulation information, e.g., current pulse amplitude levels, duty cycle, frequency and/or phase along with patient information, e.g., sensed biological data, and/or biological data entered by the patient or other operator, e.g., mood or perception of psychological state. The patient information device may analyze the stimulation information and the patient information utilizing self-learning algorithms, e.g., neural algorithms that mimic human brain function, and may modify the stimulation parameters based on the analysis.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A neuromodulation device comprising:
    electrically conductive coils arranged in an array; and
    circuitry coupled to energize the coils in the array using current pulses that generate an electromagnetic field, the circuitry configured to control one or more parameters of the current pulses, including at least amplitude and phase of the current pulses, such that the electromagnetic field undergoes constructive and destructive interference that focuses and/or steers a magnetic flux density within a region of interest of a patient and produces an electric field gradient and strength sufficient to activate one or more nerves within the region of interest while not activating nerves between the activated nerves and the electrically conductive coils.

2. The neuromodulation device of claim 1, wherein the one or more current pulse parameters further include one or more of duty cycle and frequency.

3. The neuromodulation device of claim 1, wherein the electric field has an electric field distribution spot size of at least 400 μm.

4. The neuromodulation device of claim 1, wherein the electric field strength Ex=dV/dx in the region of interest is greater than about 100 V/m.

5. The neuromodulation device of claim 1, wherein the current pulses have a maximum amplitude less than about 500 mA.

6. The neuromodulation device of claim 1, wherein each of the coils comprises a plurality of stressed elastic members.

7. The neuromodulation device of claim 6, wherein the plurality of stressed elastic members comprises:
a first stressed elastic member comprising a first anchor portion and a first free portion; and
a second stressed elastic member comprising a second anchor portion and a second free portion, wherein a stress profile in the first elastic member biases the first free portion away from a substrate and a stress profile in the second elastic member biases the second free portion away from the substrate and wherein the first free portion and the second free portion are connected together forming a loop winding.

8. The neuromodulation device of claim 1, wherein the region of interest is located at a specified depth within the patient and an electric field produced by the neuromodulation device in a region between the region of interest and the neuromodulation device is less than the electric field in the region of interest.

9. The neuromodulation device of claim 1, further comprising a flexible substrate, wherein the array of coils are disposed on the flexible substrate.

10. The neuromodulation device of claim 1, wherein the neuromodulation device is an implantable nerve cuff or a dermal patch.

11. The neuromodulation device of claim 1, further comprising energy harvesting circuitry configured to harvest power from a radio frequency (RF) signal generated by an external device and to use the harvested power to provide the current pulses.

12. The neuromodulation device of claim 1, further comprising communications circuitry configured to wirelessly transfer communication signals between the neuromodulation device and an external device.

13. The neuromodulation device of claim 12, wherein the communication signals include feedback information and the circuitry uses the feedback information to control the current pulse parameters.

14. The neuromodulation device of claim 13, wherein the feedback information is based on biological signals sensed from the patient.

15. The neuromodulation device of claim 1, wherein the circuitry includes a memory that stores one or more tables of current pulse parameter values for each coil in the array, each table corresponding to a particular profile of biological signals of the patient.

16. The neuromodulation device of claim 15, wherein the current pulse parameter values are dynamically changeable in response to a change in the biological signals.

17. A neuromodulation system comprising:
a neuromodulation device comprising:
electrically conductive coils arranged in an array; and
circuitry coupled to energize the coils in the array with current pulses that generate an electromagnetic field, the circuitry configured to control one or more parameters of the current pulses, including at least amplitude and phase of the current pulses, such that the electromagnetic field undergoes constructive and destructive interference that focuses and/or steers a magnetic flux density within a region of interest of a patient and produces an electric field gradient and strength sufficient to activate one or more nerves within the region of interest while not activating nerves between the activated nerves and the electrically conductive coils; and
communications circuitry configured to wirelessly transfer communication signals between the neuromodulation device and an external device; and
a patient information device communicatively coupled to the neuromodulation device, the patient information device configured to monitor one or more biological signals of the patient and to transfer information about the biological signals to the neuromodulation device via the communication signals.

18. The neuromodulation system of claim 17, wherein the region of interest is located at a specified depth within the patient and an electric field produced by the neuromodulation device in a region between the region of interest and the neuromodulation device is less than the electric field in the region of interest.

19. A neuromodulation method comprising:
energizing coils in an array of coils using current pulses, the current pulses generating an electromagnetic field that provides a magnetic flux density at a region of interest of a patient; and
controlling one or more parameters of the current pulses, including at least amplitude and phase, such that the electromagnetic field undergoes constructive and destructive interference that focuses and/or steers the magnetic flux density to the region of interest and produces an electric field gradient and strength sufficient to activate one or more nerves within the region of interest while not activating nerves between the activated nerves and the energized coils.

20. The method of claim 19, wherein controlling the parameters comprises dynamically changing the parameters based on biological signals sensed from the patient.

* * * * *